US011744552B2

(12) United States Patent
Takahashi et al.

(10) Patent No.: US 11,744,552 B2
(45) Date of Patent: Sep. 5, 2023

(54) ULTRASOUND DIAGNOSTIC APPARATUS, MEDICAL IMAGE PROCESSING APPARATUS, AND MEDICAL IMAGE PROCESSING METHOD

(71) Applicant: CANON MEDICAL SYSTEMS CORPORATION, Otawara (JP)

(72) Inventors: Hiroki Takahashi, Nasushiobara (JP); Takeshi Sato, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 407 days.

(21) Appl. No.: 16/243,256

(22) Filed: Jan. 9, 2019

(65) Prior Publication Data

US 2019/0209133 A1 Jul. 11, 2019

(30) Foreign Application Priority Data

Jan. 10, 2018 (JP) ................................. 2018-002178

(51) Int. Cl.
*A61B 8/00* (2006.01)
*G01S 15/89* (2006.01)
*A61B 8/08* (2006.01)

(52) U.S. Cl.
CPC .......... *A61B 8/4488* (2013.01); *A61B 8/5207* (2013.01); *A61B 8/5269* (2013.01); *A61B 8/54* (2013.01); *G01S 15/89* (2013.01)

(58) Field of Classification Search
CPC .... A61B 8/4488; A61B 8/5207; A61B 8/5269
See application file for complete search history.

(56) References Cited

U.S. PATENT DOCUMENTS

| 2008/0110261 A1* | 5/2008 | Randall ................. G01S 7/5208 |
| | | 73/592 |
| 2015/0057542 A1* | 2/2015 | Katsuyama .......... A61B 8/5269 |
| | | 600/438 |
| 2015/0320398 A1 | 11/2015 | Honjo et al. |

FOREIGN PATENT DOCUMENTS

| JP | H09-103431 A | 4/1997 |
| JP | H11-216143 A | 8/1999 |
| JP | 2007-20998 A | 2/2007 |
| JP | 2009-028366 A | 2/2009 |
| JP | 2015-226762 | 12/2015 |
| JP | 2016-002281 A | 1/2016 |
| JP | 2016-198119 | 12/2016 |

(Continued)

OTHER PUBLICATIONS

Camacho et al. ("Phase Coherence Imaging", IEE Transactions vol. 56, No. 5, 2009). (Year: 2009).*

(Continued)

*Primary Examiner* — Joseph M Santos Rodriguez
(74) *Attorney, Agent, or Firm* — Oblon, McClelland, Maier & Neustadt, L.L.P.

(57) ABSTRACT

An ultrasound diagnostic apparatus according to an embodiment includes processing circuitry configured to execute transmit aperture synthesis to conduct coherent summation on multiple received signals that are at different transmit apertures and in an identical scan line, evaluate a degree of consistency between phases of the received signals to calculate an evaluation value at each observation point, and correct a received signal having undergone the transmit aperture synthesis based on the evaluation value.

18 Claims, 9 Drawing Sheets

(56) References Cited

FOREIGN PATENT DOCUMENTS

| JP | 2017-064249 A | 4/2017 |
| JP | 2017-159028 A | 9/2017 |
| WO | WO 2017/047232 A1 | 3/2017 |

OTHER PUBLICATIONS

Camacho, J., et al. "Phase Coherence Imaging", IEEE Transactions on Ultrasonics, Ferroelectrics, and Frequency Control, vol. 56, No. 5, 2009, 15 pages.
Hasegawa, H., et al. "Effect of Subaperture Beamforming on Phase Coherence Imaging", IEEE Transactions on Ultrasonics, Ferroelectrics, and Frequency Control, vol. 61, No. 11, 2014, 12 pages.
Japanese Office Action dated Oct. 5, 2021, issued in Japanese Patent Application No. 2018-002178.
Japanese Office Action dated Apr. 19, 2022, issued in Japanese Patent Application No. 2018-002178.
Office Action dated Oct. 11, 2022, in corresponding Japanese Patent Application No. 2018-002178, 3 pages.

\* cited by examiner

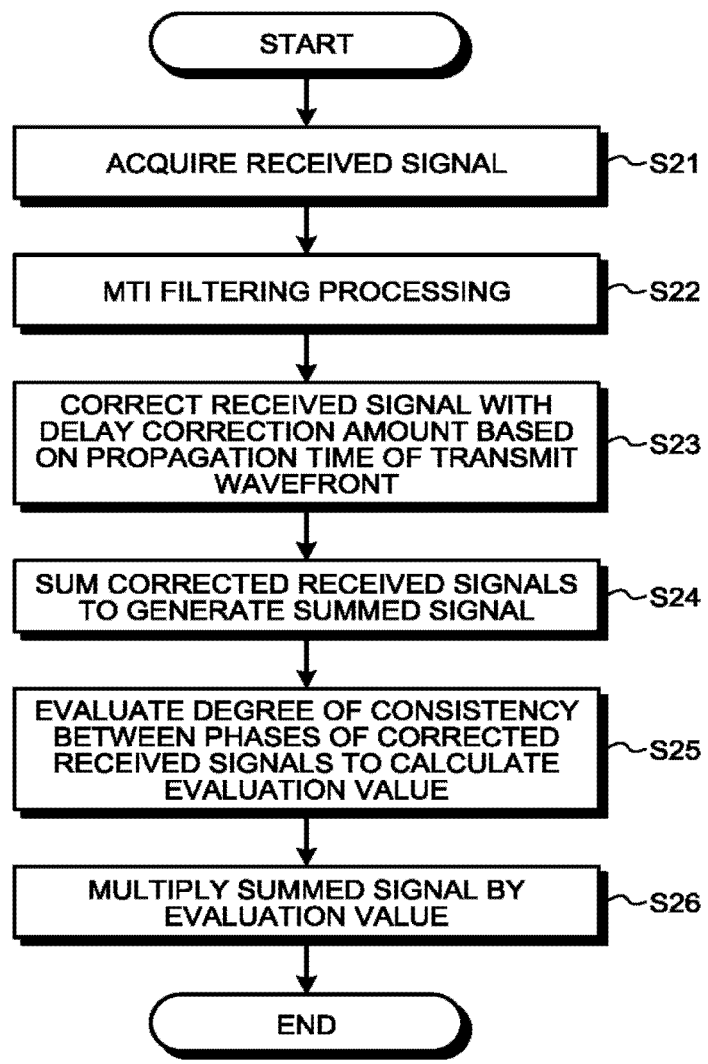

ULTRASOUND DIAGNOSTIC APPARATUS, MEDICAL IMAGE PROCESSING APPARATUS, AND MEDICAL IMAGE PROCESSING METHOD

CROSS-REFERENCE TO RELATED APPLICATIONS

This application is based upon and claims the benefit of priority from Japanese Patent Application No. 2018-2178, filed on Jan. 10, 2018; the entire contents of which are incorporated herein by reference.

FIELD

Embodiments described herein relate generally to an ultrasound diagnostic apparatus, a medical image processing apparatus, and a medical image processing method.

BACKGROUND

Ultrasound diagnostic apparatuses enable visualization of biological information by irradiating the inside of a body with ultrasound waves generated by a piezoelectric oscillator, receiving ultrasound waves reflected by or transmitted through living tissue, and generating it as an image. Ultrasound diagnostic apparatuses with real-time performance and non-invasiveness are widely used as the primary diagnosis tool for shape diagnosis or functional diagnosis of body organs.

Ultrasound probes have a plurality of piezoelectric oscillators built-in and conduct various imaging methods by controlling a delay time given to an excitation signal for driving the piezoelectric oscillators and a received signal. For example, what is called parallel simultaneous receive is conducted to form different receive directionalities during the single ultrasound transmission and set multiple receive scan lines. The parallel simultaneous receive reduces the number of times of transmissions needed to obtain one frame, whereby the frame rate may be improved.

As a way of application of the parallel simultaneous receive, a technique is used to acquire multiple receive echo signals whose transmit/receive focal points are formed at the same observation point with transmitted beams having different transmit convergence points and to execute synthesis summation. Furthermore, this technique is called transmit aperture synthesis, transmit phasing summation, or the like. The use of transmit aperture synthesis allows formation of high-accuracy transmit beam width that is even in a depth direction in addition to an improvement in S/N and therefore allows generation of ultrasound images with desired space resolution and contrast resolution. Furthermore, in such a case, there is a technique disclosed for correction on the propagation time of the transmit wavefront to an observation point for high-efficient use of transmit energy by more accurate formation of the focal point at the observation point.

BRIEF DESCRIPTION OF THE DRAWINGS

FIG. 13 is a flowchart that illustrates the steps of the transmit-aperture synthesis process by the Doppler processing circuitry according to the third embodiment.

DETAILED DESCRIPTION

An ultrasound diagnostic apparatus comprises processing circuitry. The processing circuitry is configured to execute transmit aperture synthesis to conduct coherent summation on multiple received signals that are at different transmit apertures and in an identical scan line. The processing circuitry is configured to evaluate a degree of consistency between phases of the received signals to calculate an evaluation value at each observation point. And the processing circuitry is configured to correct a received signal having undergone the transmit aperture synthesis based on the evaluation value.

With reference to drawings, an explanation is given below of the ultrasound diagnostic apparatus, a medical image processing apparatus, and a medical image processing method according to an embodiment. Although an ultrasound diagnostic apparatus of a linear scanning type is explained below, it may be an ultrasound diagnostic apparatus of a sector scanning type, a convex scanning type, or the like. Furthermore, in principle, the details described in one embodiment are also applied to other embodiments.

Figure 1:
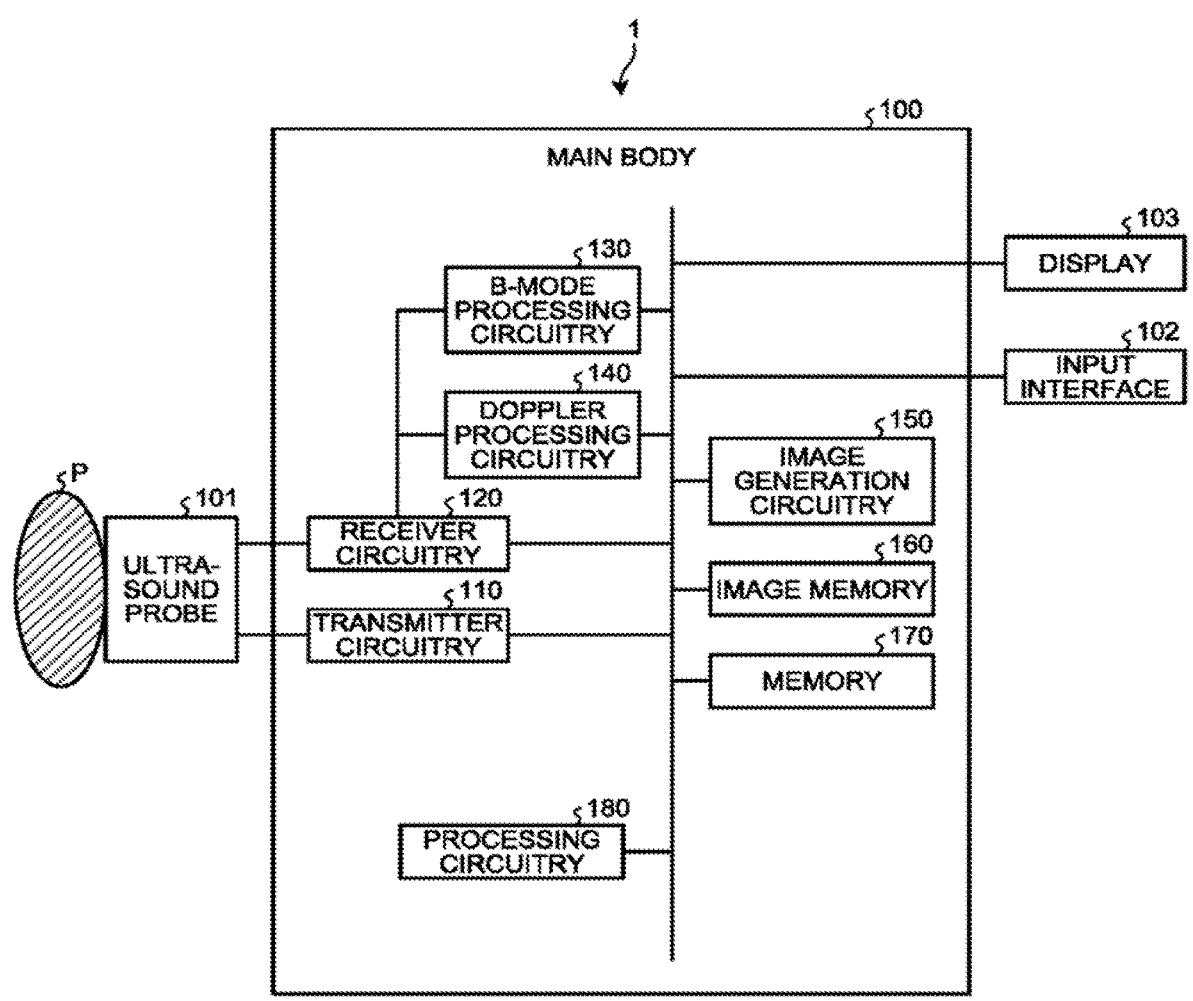
FIG. 1 is a block diagram that illustrates an example of the configuration of an ultrasound diagnostic apparatus according to a first embodiment.

FIG. 1 is a block diagram that illustrates an example of the configuration of an ultrasound diagnostic apparatus 1 according to a first embodiment. As illustrated in FIG. 1, the ultrasound diagnostic apparatus 1 according to the first embodiment includes a main body 100, an ultrasound probe 101, an input interface 102, and a display 103. Each of the ultrasound probe 101, the input interface 102, and the display 103 is connected to the main body 100.

The ultrasound probe 101 includes a plurality of oscillating elements (piezoelectric oscillators). The ultrasound probe 101 is brought into contact with the body surface of a subject P so as to transmit and receive ultrasound waves (ultrasound scan). The oscillating elements generate ultrasound waves based on drive signals fed from transmitter circuitry 110 included in the main body 100 described later. The generated ultrasound waves are reflected by the surface of mismatched acoustic impedance within the subject P and is received by the oscillating elements as reflected wave signals (received echoes) including components, or the like, scattered by a scattering substance within tissue. The ultrasound probe 101 sends reflected wave signals received by the oscillating elements to receiver circuitry 120.

In the case explained according to the present embodiment, the ultrasound probe 101 is a two-dimensional ultrasound probe (also referred to as "2D array probe") including the oscillating elements arranged in a matrix (in a grid pattern); however, this is not a limitation. For example, the ultrasound probe 101 may be a one-dimensional ultrasound probe (also referred to as "1D array probe") including oscillating elements arranged in one dimension in a predetermined direction. Furthermore, the ultrasound probe 101 may include a mechanical scanning system.

The input interface 102 includes a mouse, keyboard, button, panel switch, touch command screen, foot switch, trackball, joystick, or the like; it receives various setting requests from an operator of the ultrasound diagnostic apparatus 1 and transfers received various setting requests to the main body 100.

The display 103 presents a GUI (Graphical User Interface) for the operator of the ultrasound diagnostic apparatus 1 to input various setting requests by using the input interface 102 and presents ultrasound image data, or the like, generated by the main body 100. For example, the display 103 is composed of a liquid crystal display, CRT (Cathode Ray Tube) display, or the like. Furthermore, the display 103 is referred to as a monitor when needed.

The main body 100 is an apparatus that generates ultrasound image data based on reflected wave signals received by the ultrasound probe 101. As illustrated in FIG. 1, the main body 100 includes, for example, the transmitter circuitry 110, the receiver circuitry 120, B-mode processing circuitry 130, Doppler processing circuitry 140, image generation circuitry 150, an image memory 160, memory 170, and processing circuitry 180. The transmitter circuitry 110, the receiver circuitry 120, the B-mode processing circuitry 130, the Doppler processing circuitry 140, the image generation circuitry 150, the image memory 160, the memory 170, and the processing circuitry 180 are communicatively connected to each other.

The transmitter circuitry 110 includes pulsar circuitry, or the like. The pulsar circuitry repeatedly generates rate pulses to form transmit ultrasound waves at a predetermined rate frequency (PRF: pulse repetition frequency) and outputs the generated rate pulse to the ultrasound probe 101.

Furthermore, the transmitter circuitry 110 outputs the value of the amplitude of a drive signal output from the pulsar circuitry under the control of the processing circuitry 180. Moreover, the transmitter circuitry 110 transmits, to the ultrasound probe 101, the delay amount that corresponds to an ultrasound wave transmitted from the ultrasound probe 101 under the control of the processing circuitry 180. Specifically, the transmitter circuitry 110 feeds a predetermined delay amount to a drive signal based on a command from the processing circuitry 180 and applies it to the ultrasound probe 101 so as to give a desired directional characteristic (e.g., converged beam) to a transmitted ultrasound wave. Furthermore, with regard to the directional characteristics, the transmitter circuitry 110 may transmit plane-wave ultrasound waves or diffuse-wave ultrasound waves (ultrasound waves over a wide range similar to transmission of plane-wave ultrasound waves).

The receiver circuitry 120 includes an A/D converter and a receive beamformer. After the receiver circuitry 120 receives a reflected wave signal output from the ultrasound probe 101, the A/D converter first converts the reflected wave signal into digital data, and the receive beamformer executes a phasing-summing process on digital data from each of the channels to generate reflected wave data and transmits the generated reflected wave data to the B-mode processing circuitry 130 and the Doppler processing circuitry 140. Furthermore, the details of the receiver circuitry 120 are given later. Moreover, reflected wave data is also referred to as a received signal.

The B-mode processing circuitry 130 performs various types of signal processing on reflected wave data output from the receiver circuitry 120. The B-mode processing circuitry 130 conducts envelope detection processing, logarithmic compression, or the like, on reflected wave data to generate data (B-mode data) representing the signal intensity at each sample point (observation point) with brightness of the pixel. The B-mode processing circuitry 130 feeds the generated B-mode data to the image memory 160.

The Doppler processing circuitry 140 acquires reflected wave data from the receiver circuitry 120 and generates data (Doppler data) by extracting kinetic information based on the Doppler effect of a movable object from the acquired reflected wave data at each sample point within a scan area. For example, the Doppler processing circuitry 140 generates Doppler data by executing frequency analysis on velocity information on a movable object, extracting a blood flow, tissue, or contrast-agent echo component due to the Doppler effect, and extracting movable-object information, such as the average velocity, variance, or power, at multiple points. Here, kinetic information on a movable object refers to average velocity, variance value, power value, or the like. Furthermore, here, the movable object is, for example, a blood flow, tissue such as wall of the heart, or contrast agent.

The image generation circuitry 150 generates ultrasound image data from data generated by the B-mode processing circuitry 130 and the Doppler processing circuitry 140. The image generation circuitry 150 generates B-mode image data representing the intensity of a reflected wave with brightness from the B-mode data generated by the B-mode processing circuitry 130. Furthermore, the image generation circuitry 150 generates Doppler image data representing movable object information from Doppler data generated by the Doppler processing circuitry 140. Doppler image data is velocity image data, variance image data, power image data, or image data with a combination thereof.

Here, typically, the image generation circuitry 150 converts (scan conversion) a scan-line signal sequence for ultrasound scanning into a scan-line signal sequence in a video format for typically televisions, or the like, and generates ultrasound image data for display. Specifically, the image generation circuitry 150 conducts coordinate transform in accordance with a scanning form of ultrasound waves by the ultrasound probe 101 so as to generate ultrasound image data for display. Furthermore, other than scan conversion, the image generation circuitry 150 conducts various types of image processing, for example, by using multiple image frames having undergone scan conversion, image processing (smoothing processing) to regenerate an image with the average value of brightness, image processing (edge enhancement processing) using a differential filter within an image, or the like. Furthermore, the image generation circuitry 150 synthesizes ultrasound image data with textual information on various parameters, scale marks, body marks, and the like.

The image memory 160 is a memory that stores image data (B-mode image data, Doppler image data, or the like) generated by the image generation circuitry 150. Furthermore, the image memory 160 may store data generated by the B-mode processing circuitry 130 and the Doppler processing circuitry 140. B-mode data and Doppler data stored in the image memory 160 may be invoked by, for example, an operator, and it becomes ultrasound image data for display after being passed through the image generation circuitry 150.

The memory 170 stores control programs for conducting ultrasound transmission/reception, image processing, display processing, and the like, diagnosis information (e.g., patient ID or doctor's observations), diagnosis protocols, and various types of data such as various body marks. Furthermore, the memory 170 is used as needed to store image data, or the like, which is stored in the image memory 160. Moreover, data stored in the memory 170 may be transferred to an external device via an undepicted communication interface.

The processing circuitry 180 controls the entire process of the ultrasound diagnostic apparatus 1. Specifically, the processing circuitry 180 controls processes of the transmitter circuitry 110, the receiver circuitry 120, the B-mode processing circuitry 130, the Doppler processing circuitry 140, the image generation circuitry 150, and the like, based on various setting requests input from the operator via the input interface 102 and various control programs and various types of data read from the memory 170. Furthermore, the processing circuitry 180 controls the ultrasound probe 101 via the transmitter circuitry 110 and the receiver circuitry 120 so as to execute transmit aperture synthesis. Moreover, the processing circuitry 180 causes the display 103 to present ultrasound image data stored in the image memory 160 or the memory 170.

Furthermore, the transmitter circuitry 110, the receiver circuitry 120, the B-mode processing circuitry 130, the Doppler processing circuitry 140, the image generation circuitry 150, and the processing circuitry 180 built in the main body 100 are composed of the hardware of a processor (CPU (Central Processing Unit), MPU (Micro-Processing Unit), integrated circuit, or the like). Moreover, the transmitter circuitry 110, the receiver circuitry 120, and the like, built in the main body 100 are composed of the hardware of an integrated circuit, or the like, in some cases, while in other cases it is a modular software program.

Figure 2:
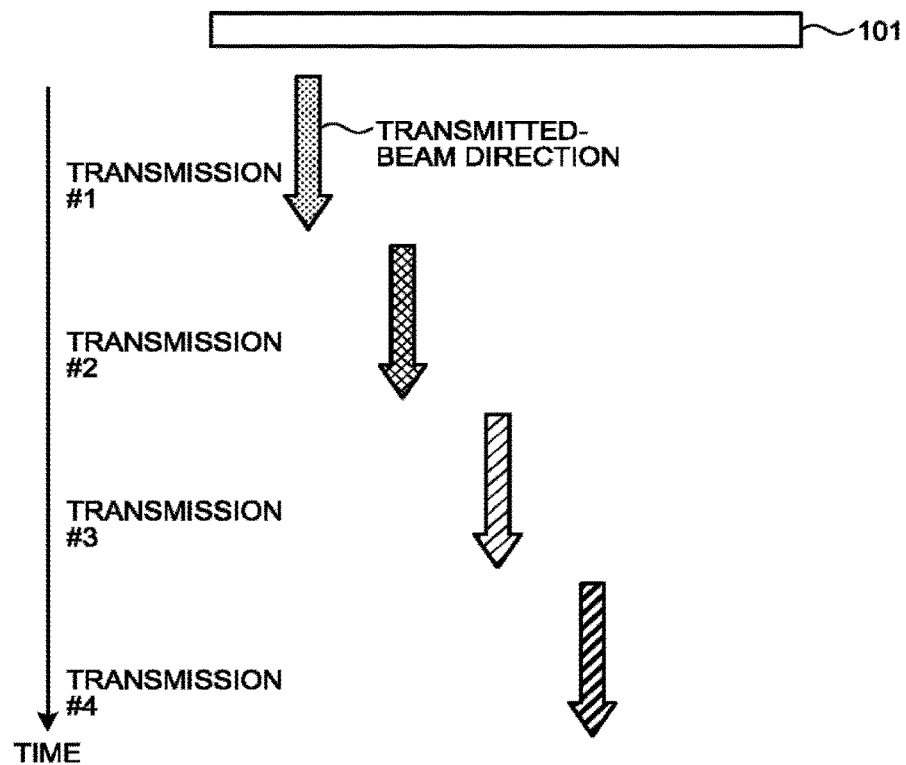
FIG. 2 is a diagram that illustrates transmit aperture synthesis.
Figure 3:
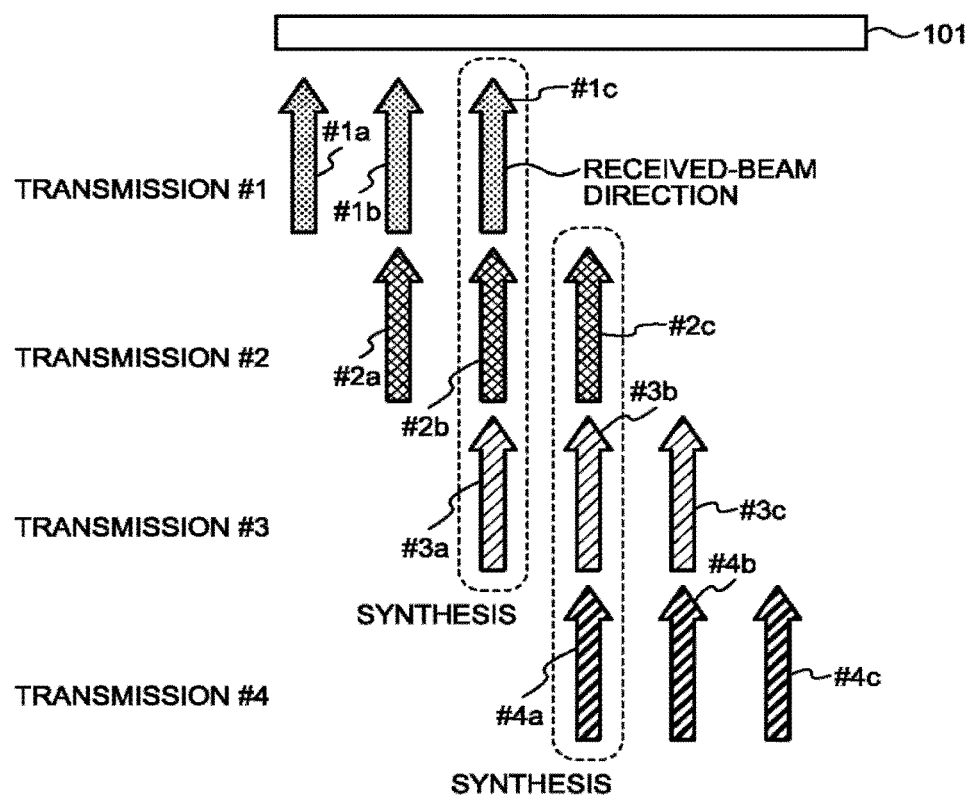
FIG. 3 is a diagram that illustrates transmit aperture synthesis.

The ultrasound diagnostic apparatus 1 having the above configuration sometimes generates ultrasound images by using transmit aperture synthesis. FIGS. 2 and 3 are diagrams that illustrate transmit aperture synthesis. FIG. 2 illustrates operation of transmit control. In the case illustrated in FIG. 2, the ultrasound probe 101 transmits ultrasound waves four times in order of transmission #1, transmission #2, transmission #3, and transmission #4 by shifting the transmit focus by one element.

FIG. 3 illustrates operation of receive control. In the case illustrated in FIG. 3, with regard to each ultrasound transmission from the transmission #1 to the transmission #4, reflected wave signals are received by three elements of the ultrasound probe 101 and three received signals are generated. Specifically, the ultrasound diagnostic apparatus 1 generates a received signal #1a, a received signal #1b, and a received signal #1c with regard to the ultrasound transmission in the transmission #1. Furthermore, the ultrasound diagnostic apparatus 1 generates a received signal #2a, a received signal #2b, and a received signal #2c with regard to the ultrasound transmission in the transmission #2. In the same manner, the ultrasound diagnostic apparatus 1 generates a received signal #3a, a received signal #3b, and a received signal #3c with regard to the ultrasound transmission in the transmission #3. Moreover, the ultrasound diagnostic apparatus 1 generates a received signal #4a, a received signal #4b, and a received signal #4c with regard to the ultrasound transmission in the transmission #4.

Then, the ultrasound diagnostic apparatus 1 synthesizes received signals in the same channel, obtained during different transmissions. For example, as illustrated in FIG. 3, the ultrasound diagnostic apparatus 1 synthesizes the received signal #1c, the received signal #2b, and the received signal #3a that are at different transmit apertures and in the identical scan line. Furthermore, for example, the ultrasound diagnostic apparatus 1 synthesizes the received signal #2c, the received signal #3b, and the received signal #4a that are at different transmit apertures and in the identical scan line.

Here, as for transmit aperture synthesis, the more different the incident angle of the transmit wavefront, the higher the space resolution and the better the S/N may be expected. However, in the actual operation, there is a limitation in making the incident angle of the transmit wavefront different as the imaging area of an ultrasound image is deep with respect to the transmit aperture plane. Therefore, there is a demand for the technique that improves the space resolution under the condition that it is difficult to sufficiently change the incident angle of the transmit wavefront in transmissions.

For ultrasound imaging using the ultrasound probe 101 having oscillating elements arrayed therein, a beam-forming technique actively using coherence between the elements has been developed. For example, there is a disclosed beam-forming technique that reduces noises during transmissions with an aperture synthesis method by using a restricted error minimization method that uses a correlation matrix of received signals during different transmissions. However, this beam-forming technique has a low stability because of the need of inverse matrix calculation, a high calculation load, the possibility of divergence in solutions, and the like.

Figure 4:
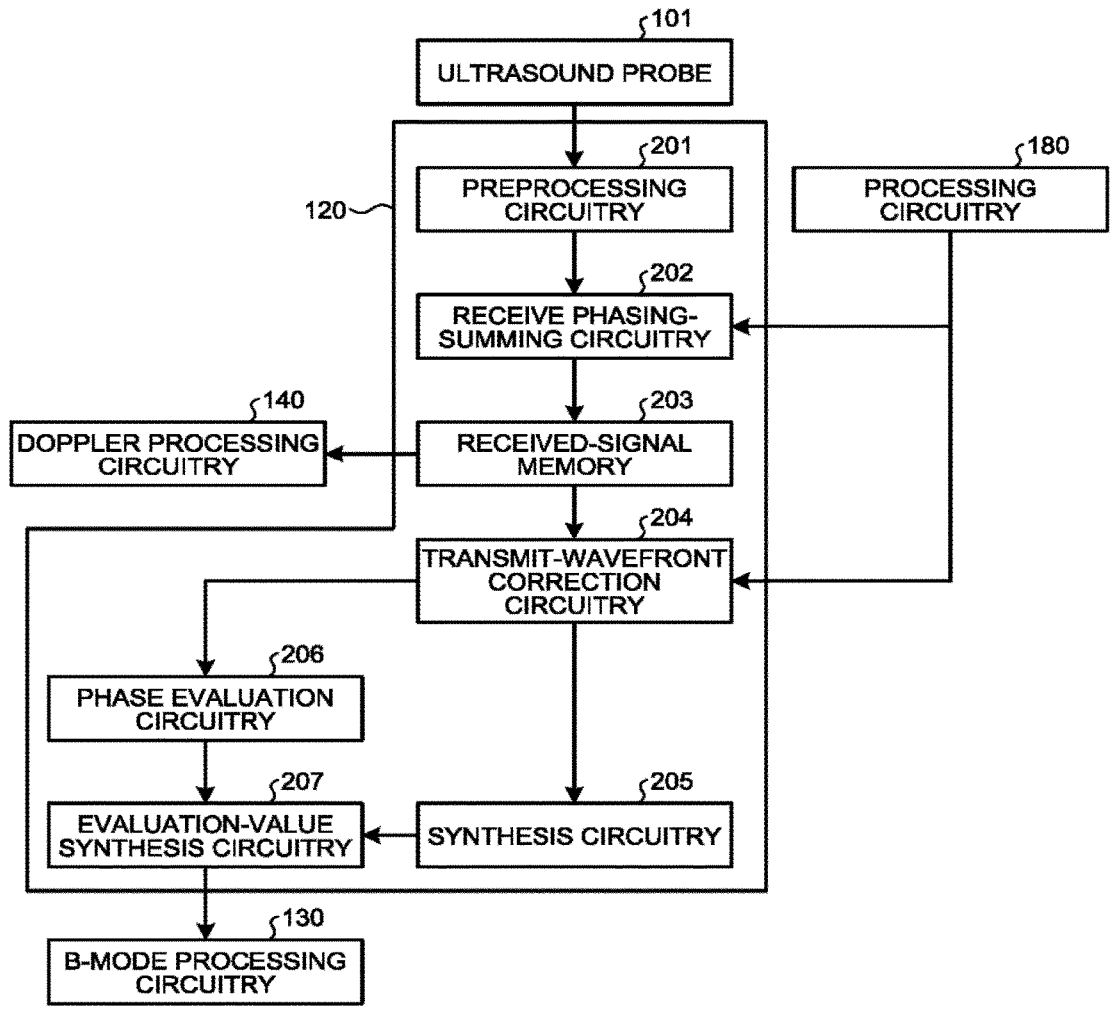
FIG. 4 is a block diagram that illustrates an example of the configuration of receiver circuitry according to the first embodiment.
Figure 5:
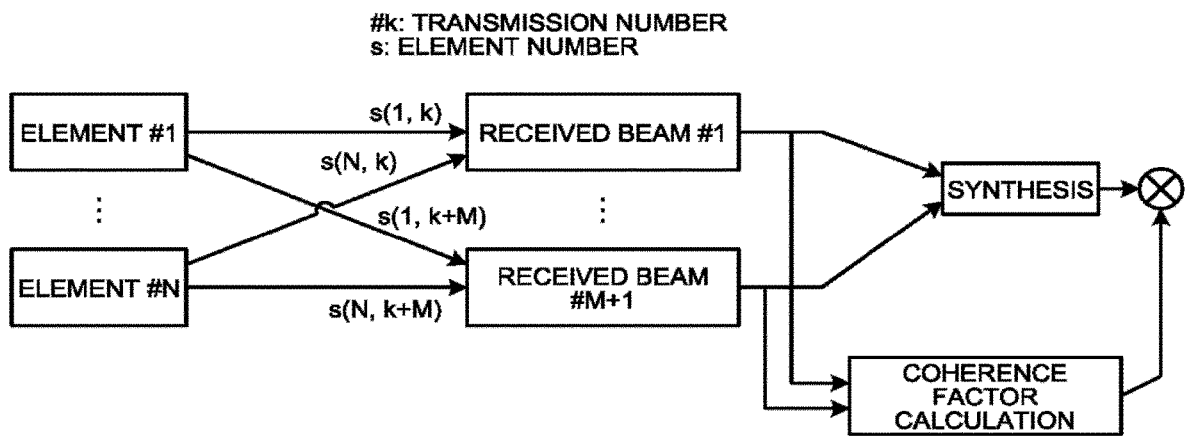
FIG. 5 is a diagram that illustrates the first embodiment.
Figure 6:
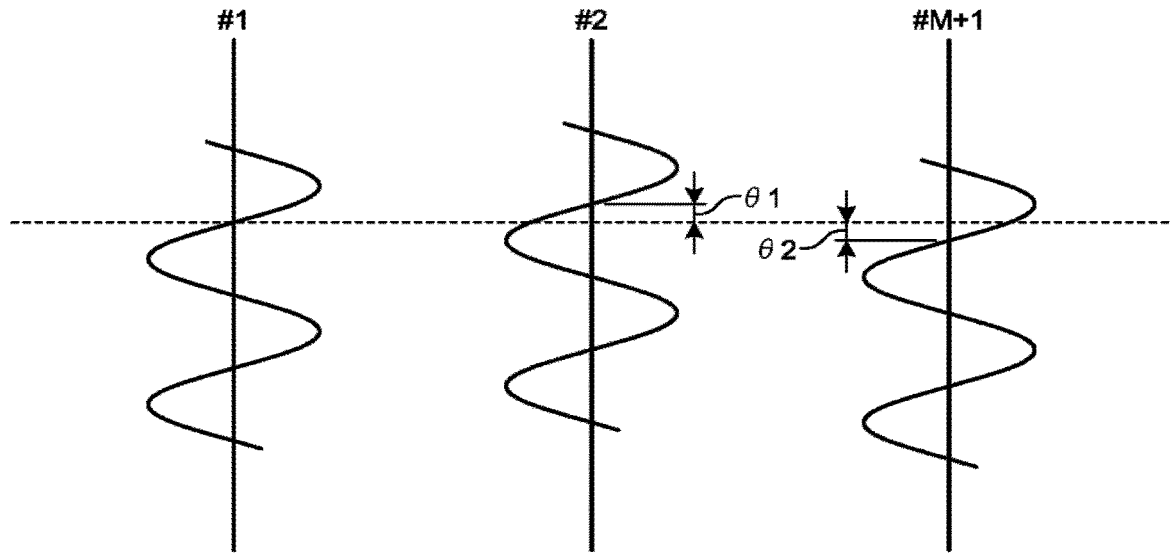
FIG. 6 is a diagram that illustrates the first embodiment.

Therefore, the ultrasound diagnostic apparatus 1 according to the first embodiment executes a transmit-aperture synthesis process described below to obtain ultrasound images with an improved space resolution. The transmit-aperture synthesis process is performed by the receiver circuitry 120. With reference to FIGS. 4 to 6, the receiver circuitry 120 according to the first embodiment is explained in detail. FIG. 4 is a block diagram that illustrates an example of the configuration of the receiver circuitry 120 according to the first embodiment, and FIGS. 5 and 6 are diagrams that illustrate the first embodiment.

As illustrated in FIG. 4, the receiver circuitry 120 according to the first embodiment includes preprocessing circuitry 201, receive phasing-summing circuitry 202, received-signal memory 203, transmit-wavefront correction circuitry 204, synthesis circuitry 205, phase evaluation circuitry 206, and evaluation-value synthesis circuitry 207.

The preprocessing circuitry 201 includes for example, amplifier circuitry (referred to as "amp" when needed), an A/D (Analog/Digital) converter (referred to as "ADC" when needed), and quadrature detection circuitry (referred to as "IQ" when needed). The amplifier circuitry performs a gain compensation process by amplifying a reflected wave signal received by the ultrasound probe 101 on a per-channel basis. The A/D converter conducts A/D conversion on the reflected wave signal having undergone gain compensation. The quadrature detection circuitry converts the reflected wave signal having undergone A/D conversion into an in-phase signal (I signal, I: In-phase) and a quadrature signal (Q signal, Q: Quadrature-phase) in a baseband.

The receive phasing-summing circuitry 202 performs a summing process by giving a predetermined delay time to a reflected wave signal received by the ultrasound probe 101 to apply a convergence directional characteristic and generates a received signal in which a reflected echo component from a predetermined position is enhanced. During the summing process, the receive phasing-summing circuitry 202 receives a setting condition from the processing circuitry 180 and performs a process in accordance with the received condition. Here, the setting condition is, for example, the number of receive aperture channels, apodization function, or the number of parallel simultaneous receptions.

FIG. 5 illustrates received signals that are obtained during different transmissions with respect to each position from an element #1 to an element #N. Furthermore, the received signal is also referred to as a received beam. For example, the receive phasing-summing circuitry 202 generates a received beam #1 from the reflected wave signal received by the element #1 during k-th transmission, generates a received beam #2 from the reflected wave signal received by the element #1 during k+l-th transmission, and generates a received beam #M+1 from the reflected wave signal received by the element #1 during k+M-th transmission. In the same manner, the receive phasing-summing circuitry 202 generates the received beam #1 from the reflected wave signal received by the element #N during k-th transmission, generates the received beam #2 from the reflected wave signal received by the element #N during k+l-th transmission, and generates the received beam #M+1 from the reflected wave signal received by the element #N during k+M-th transmission.

The receive phasing-summing circuitry 202 stores a received signal having undergone phasing summation in the received-signal memory 203. The received-signal memory 203 stores received signals obtained during different transmissions with regard to each receive scan line.

The transmit-wavefront correction circuitry 204 corrects multiple received signals with a delay amount based on the propagation time of the transmit wavefront. For example, the transmit-wavefront correction circuitry 204 applies a delay correction amount to a received signal, stored in the received-signal memory 203, based on the propagation time of the transmit wavefront. Here, the propagation time of the transmit wavefront is the time to reach the receive focal point with regard to an element that transmits an ultrasound wave.

For example, the transmit-wavefront correction circuitry 204 obtains the propagation time of the transmit wavefront in accordance with the setting condition received from the processing circuitry 180. Here, the setting condition is, for example, the number of transmit aperture channels, apodization function, or focus position. Here, the transmit-wavefront correction circuitry 204 may use, as the method for calculating a delay correction amount, the correction method disclosed in Japanese Laid-open Patent Publication No. 2009-240700 or the correction method disclosed in WO2016-132924. Here, the correction method disclosed in Japanese Laid-open Patent Publication No. 2009-240700 is a correction method that, without using a wavefront model, calculates the propagation time of an ultrasound wave transmitted from each oscillating element and determines a correction amount based on the distribution of propagation times. Furthermore, the correction method disclosed in WO2016-132924 is a correction method based on a wavefront model in which the transmit focal point is a virtual point sound source. Here, the transmit-wavefront correction circuitry 204 is an example of a correcting unit.

The synthesis circuitry 205 conducts transmit aperture synthesis to perform coherent summation on multiple received signals that are at different transmit apertures and in the identical scan line. For example, the synthesis circuitry 205 conducts transmit aperture synthesis to perform coherent summation on multiple received signals that have been corrected by the transmit-wavefront correction circuitry 204. Specifically, the synthesis circuitry 205 sums output signals from the transmit-wavefront correction circuitry 204 and outputs a summed signal.

More specifically, the synthesis circuitry 205 synthesizes the received beam #1, the received beam #2, and the received beam #M+1, generated from the element #1 illustrated in FIG. 5. Furthermore, the synthesis circuitry 205 synthesizes the received beam #1, the received beam #2, and the received beam #M+1, generated from the element #N illustrated in FIG. 5. Here, the synthesis circuitry 205 is an example of a transmit-aperture synthesizing unit.

The phase evaluation circuitry 206 evaluates the degree of consistency between phases of received signals to calculate an evaluation value at each observation point. For example, the phase evaluation circuitry 206 evaluates the degree of consistency between phases of corrected received signals to calculate an evaluation value. In other words, the phase evaluation circuitry 206 evaluates the degree of consistency between phases with regard to received signals which are at the identical receive scan line and for which the transmit wavefront has been corrected.

More specifically, the phase evaluation circuitry 206 evaluates the degree of consistency between phases of received beams generated from the element #1 illustrated in FIG. 5. For example, the phase evaluation circuitry 206 evaluates the degree of consistency among the phases of the received beam #1, the received beam #2, and the received beam #M+1 of the element #1 illustrated in FIG. 5. In the same manner, the phase evaluation circuitry 206 evaluates the degree of consistency between phases of received beams generated from the element #N illustrated in FIG. 5.

More specifically, as illustrated in FIG. 6, the phase evaluation circuitry 206 evaluates the degree of consistency between the phases of the received signals #1, #2, and #M+1. In the example illustrated in FIG. 6, when the received signal #1 is a reference, the received signal #2 is shifted from the received signal #1 by 01, and the received signal #M+1 is shifted from the received signal #1 by 02. That is, the phase evaluation circuitry 206 evaluates the degree of dispersion of the phases of received signals. Here, the phase evaluation circuitry 206 evaluates the degree of consistency between phases by using Equation (1) disclosed in for example Non Patent Literature 1 (J. Camacho, M. Parrilla, and C. Fritsch, Phase Coherence Imaging, IEEE Trans Ultrason Ferroelectr Freq Control, 2009, 56(5):958-74).

$$PCF = 1 - \gamma \frac{\sigma}{\sigma_0} \qquad (1)$$

In Equation (1), σ, σ0, and γ represent the standard deviation of the phase of a received signal, a normalization coefficient (e.g., standard deviation in Gaussian distribution), and an adjustment coefficient, respectively. Furthermore, the evaluation method for the phase evaluation circuitry 206 is not limited to the above-described Equation (1). For example, the phase evaluation circuitry 206 may evaluate the degree of consistency between phases by using any method as long as an evaluation function outputs a higher value as the dispersion of phases of received signals is smaller (the degree of consistency is higher). Moreover, the phase evaluation circuitry 206 may evaluate the degree of consistency between phases with regard to each frequency component by, for example, conducting Fourier transform on received signals and evaluating the amplitude of the cross-spectrum of the received signals. Here, the phase evaluation circuitry 206 is an example of a calculating unit.

The evaluation-value synthesis circuitry 207 corrects a received signal having undergone transmit aperture synthesis based on an evaluation value. For example, the evaluation-value synthesis circuitry 207 multiplies the received signal, which has undergone transmit aperture synthesis and output from the synthesis circuitry 205, by the evaluation value which corresponds to the degree of consistency between the phases and output from the phase evaluation circuitry 206.

More specifically, the evaluation-value synthesis circuitry 207 corrects the received beam having undergone aperture synthesis from the element #1 illustrated in FIG. 5 with the evaluation value for the element #1 illustrated in FIG. 5. Furthermore, the receiver circuitry 120 corrects the received beam having undergone aperture synthesis from the element #N illustrated in FIG. 5 with the evaluation value for the element #N illustrated in FIG. 5. Furthermore, the evaluation-value synthesis circuitry 207 may not only multiply but also add a received signal and an evaluation value after they are multiplied by a coefficient. Here, the evaluation-value synthesis circuitry 207 is an example of a signal processing unit.

Then, the B-mode processing circuitry 130 performs an envelope detection process, or the like, on a received signal, thereby generating B-mode data. Then, the image generation circuitry 150 generates ultrasound image data from B-mode data generated by the B-mode processing circuitry 130.

Figure 7:
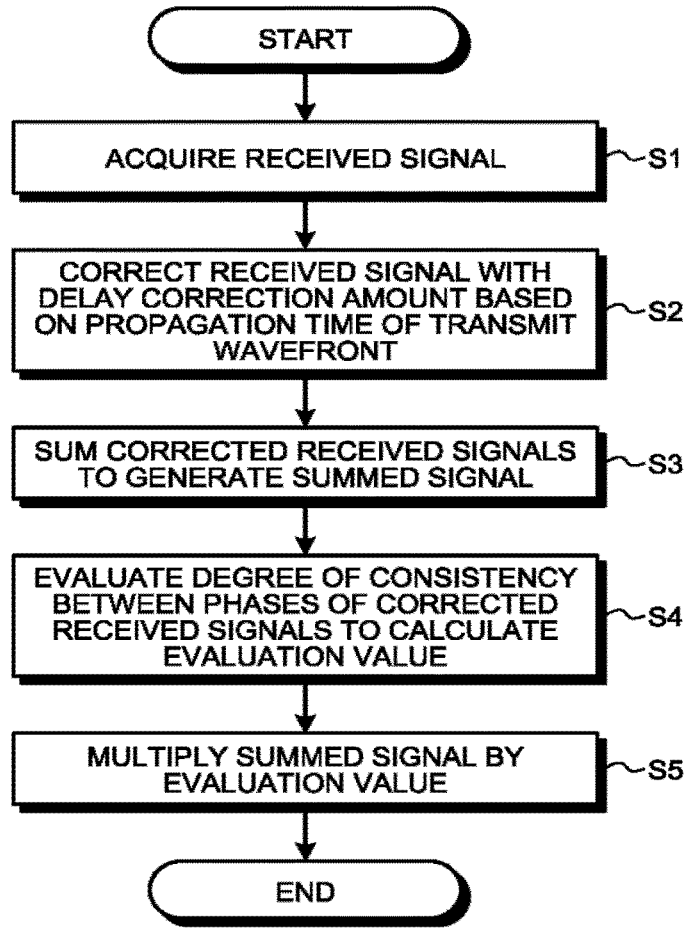
FIG. 7 is a flowchart that illustrates the steps of a transmit-aperture synthesis process by the receiver circuitry according to the first embodiment.

FIG. 7 is a flowchart that illustrates the steps of a transmit-aperture synthesis process by the receiver circuitry 120 according to the first embodiment. FIG. 7 illustrates the flowchart that explains operation of the receiver circuitry 120. Step S1 to Step S2 are steps performed by the transmit-wavefront correction circuitry 204. At Step S1, the transmit-wavefront correction circuitry 204 acquires a received signal from the received-signal memory 203. At Step S2, the transmit-wavefront correction circuitry 204 corrects a received signal with a delay correction amount based on the propagation time of the transmit wavefront.

Step S3 is a step performed by the synthesis circuitry 205. At Step S3, the synthesis circuitry 205 sums corrected received signals to generate a summed signal. Step S4 is a step performed by the phase evaluation circuitry 206. At Step S4, the phase evaluation circuitry 206 evaluates the degree of consistency between the phases of the corrected received signals to calculate an evaluation value. Step S5 is a step performed by the evaluation-value synthesis circuitry 207. At Step S5, the evaluation-value synthesis circuitry 207 multiplies the summed signal by the evaluation value.

In this way, the ultrasound diagnostic apparatus 1 according to the first embodiment evaluates the degree of consistency between the phases of received signals to calculate an evaluation value at each observation point and corrects the received signal having undergone transmit aperture synthesis based on the evaluation value. That is, the phases of received signals obtained during different transmissions and in the identical scan line are evaluated, and the received signal having undergone aperture synthesis is corrected based on the evaluation value so that an ultrasound image is generated. Thus, according to the first embodiment, ultrasound images with an improved space resolution may be obtained.

Furthermore, Non Patent Literature 1 discloses a technique of evaluating the degree of consistency between the phases of element received signals having undergone receive phasing and superimposing it with the signal having undergone phasing summation. The technique improves a resolution in an orientation direction but has a problem of suppression of the intensity in a speckle area of an image. It has been pointed out that one of the causes of this problem is improper evaluation of a phase at an observation point because a signal for evaluating a phase is not converged for receiving.

Furthermore, Non Patent Literature 2 (H. Hasegawa and H. Kanai, Effect of sub-aperture beamforming on phase coherence imaging, IEEE Trans Ultrason Ferroelectr Freq Control, 2014, 61(11):1779-90) discloses a technique of conducting receive phasing summation with regard to multiple sub-apertures and, for signals received and converged at observation points, evaluating the degree of consistency between the phases. This technique, however, has relatively low convergence characteristics of sub-aperture receive signals due to division of receive aperture. Conversely, as the ultrasound diagnostic apparatus 1 according to the first embodiment uses received signals during transmissions, there is no need to divide a receive aperture. For this reason, a received signal for evaluating a phase may be obtained at an observation point more selectively.

Furthermore, Patent Literature 1 discloses a technique of using an adaptive beamformer in the MV method (minimum variance) or the APES method to calculate a weight coefficient applied to received signals in transmissions with the adaptive beamformer. According to Patent Literature 1, the obtained weighting function is applied to a received signal and then transmit aperture synthesis is executed, whereby it is possible to obtain signals with suppressed system noises, or the like, which are incoherent in transmissions. This technique, however, has a problem of an increase in calculation costs and divergence in solutions as the adaptive beamformer needs to calculate an inverse matrix.

Conversely, the ultrasound diagnostic apparatus 1 according to the first embodiment does not need to calculate an inverse matrix. For this reason, the ultrasound diagnostic apparatus 1 according to the first embodiment has low calculation processing load and high calculation stability. That is, the first embodiment eliminates the problems of an increase in calculation costs and divergence in solutions as there is no use of inverse matrix calculations, and allows an improvement in the resolution and the contrast of ultrasound images.

Figure 8:
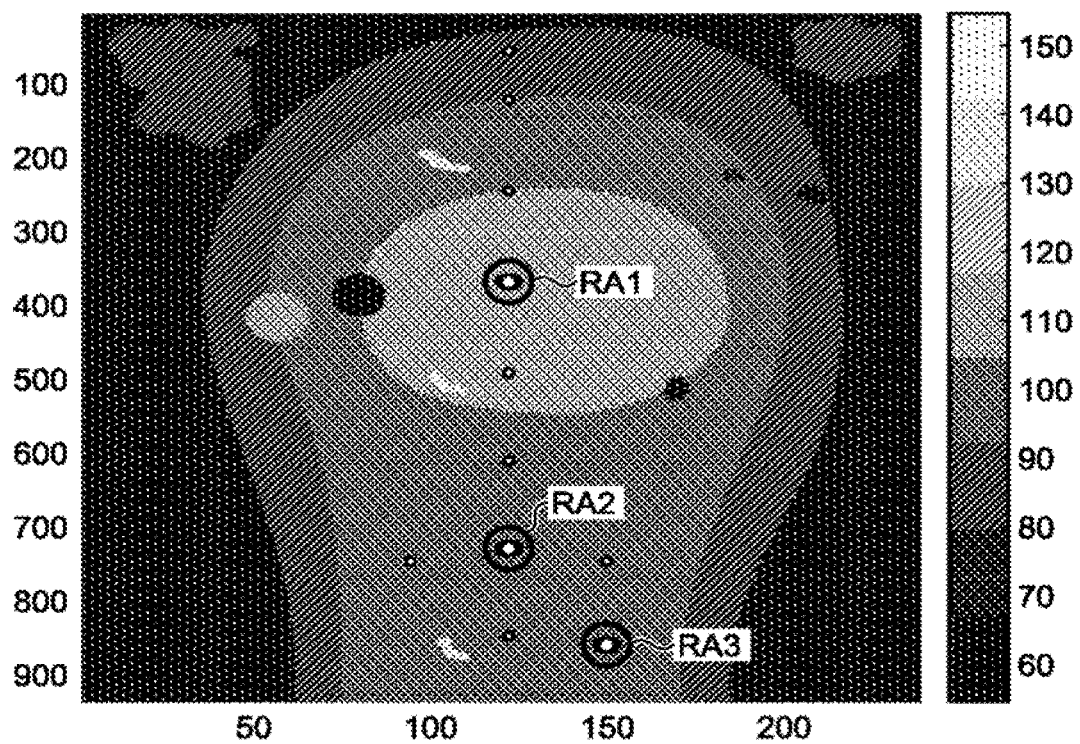
FIG. 8 is a diagram that illustrates the first embodiment.
Figure 9:
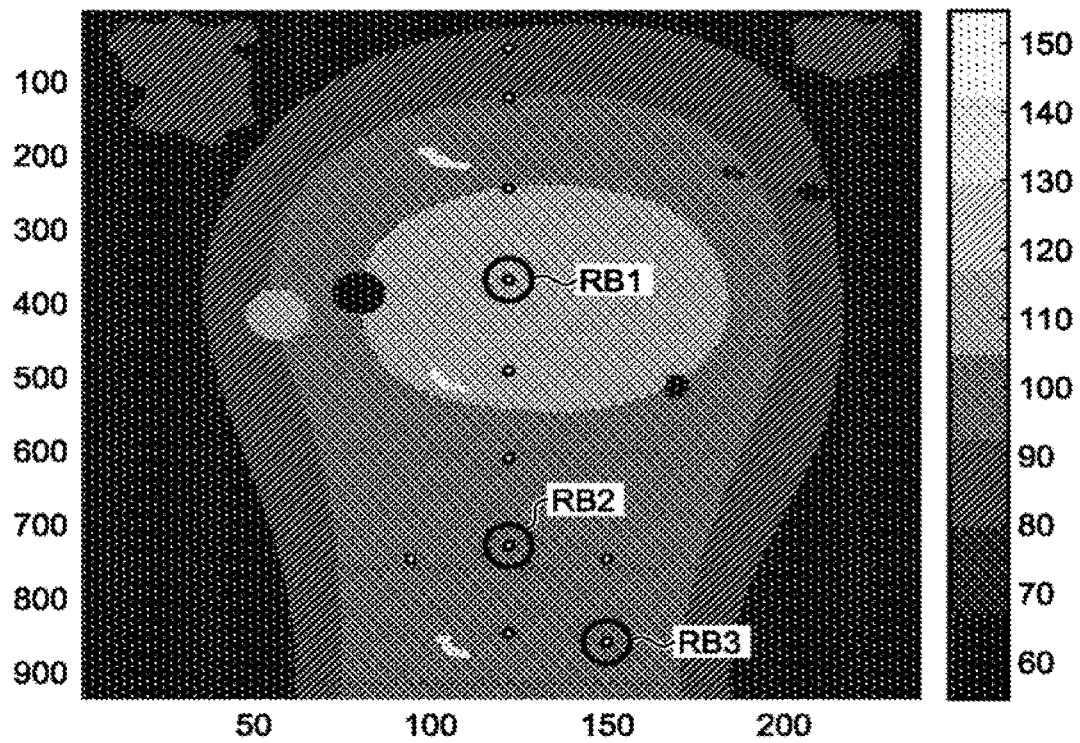
FIG. 9 is a diagram that illustrates the first embodiment.

FIGS. 8 and 9 are diagrams that illustrate the first embodiment. FIG. 8 illustrates a case where a received signal having undergone transmit aperture synthesis has not been corrected with an evaluation value, and FIG. 9 illustrates a case where a received signal having undergone transmit aperture synthesis has been corrected with an evaluation value. In FIG. 8, ranges (RA1, RA2, RA3) surrounded by circles have noticeable blur particularly in a horizontal direction. Conversely, as illustrated in regions (RB1, RB2, RB3) surrounded by circles in FIG. 9, as a defect in a cyst in the depth has been improved and wire echo has been narrowed in an orientation direction, a difference from the background in brightness is noticeable. Here, the regions RB1, RB2, and RB3 surrounded by circles illustrated in FIG. 9 correspond to the regions RA1, RA2, and RA3 surrounded by circles illustrated in FIG. 8, respectively.

Currently, imaging of harmonic components is widely practiced (what is called harmonic imaging). Known as typical harmonic imaging are contrast harmonic imaging (CHI) for imaging harmonics generated due to a contrast agent, and tissue harmonic imaging (THI) for imaging harmonic components accumulated in the process of propagation of ultrasound waves through tissue. Known as a scanning method for CHI or THI are an amplitude modulation (AM) method, a phase modulation (PM) method called "pulse subtraction method" or "pulse inversion method", or an AMPM method that produces the advantages of both the AM method and the PM method by combining their scanning methods. Therefore, in the second embodiment, an explanation is given of a case where a transmit-aperture synthesis process is applied to the above harmonic imaging.

Figure 10:
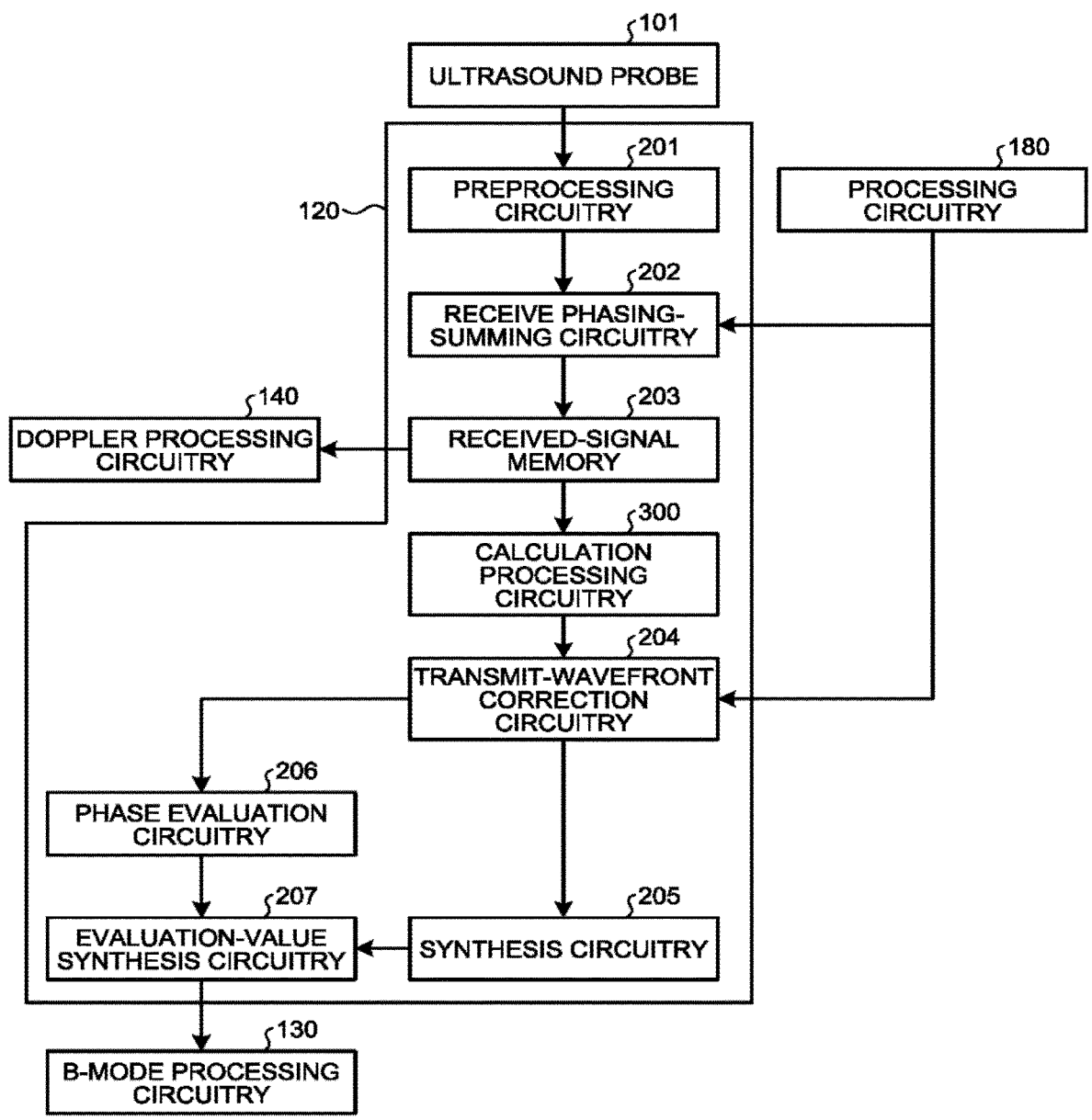
FIG. 10 is a block diagram that illustrates an example of the configuration of the receiver circuitry according to a second embodiment.

An example of the configuration of an ultrasound diagnostic apparatus according to the second embodiment is the same as the ultrasound diagnostic apparatus 1 according to the first embodiment illustrated in FIG. 1 except that the configuration of part of the receiver circuitry 120 is different. FIG. 10 is a block diagram that illustrates an example of the configuration of the receiver circuitry 120 according to the second embodiment. Furthermore, an example of the configuration of the receiver circuitry 120 according to the second embodiment illustrated in FIG. 10 is the same as an example of the configuration of the receiver circuitry 120 according to the first embodiment illustrated in FIG. 4 except that calculation processing circuitry 300 is further included. Therefore, in the second embodiment, the calculation processing circuitry 300 is explained in detail.

Furthermore, according to the second embodiment, the processing circuitry 180 controls the ultrasound probe 101 via the transmitter circuitry 110 so as to conduct multiple times of transmissions by modulating the amplitude or the phase of ultrasound waves to be transmitted. For example, in the AM method, the PM method, and the AMPM method, the processing circuitry 180 controls the ultrasound probe 101 via the transmitter circuitry 110 so as to conduct multiple times of ultrasound transmissions with different amplitudes and phases with respect to the identical scan line.

As illustrated in FIG. 10, the receiver circuitry 120 according to the second embodiment includes the preprocessing circuitry 201, the receive phasing-summing circuitry 202, the received-signal memory 203, the transmit-wavefront correction circuitry 204, the synthesis circuitry 205, the phase evaluation circuitry 206, the evaluation-value synthesis circuitry 207, and the calculation processing circuitry 300.

The preprocessing circuitry 201, the receive phasing-summing circuitry 202, the received-signal memory 203, the transmit-wavefront correction circuitry 204, the synthesis circuitry 205, the phase evaluation circuitry 206, and the evaluation-value synthesis circuitry 207 included in the receiver circuitry 120 according to the second embodiment correspond to the preprocessing circuitry 201, the receive phasing-summing circuitry 202, the received-signal memory 203, the transmit-wavefront correction circuitry 204, the synthesis circuitry 205, the phase evaluation circuitry 206, and the evaluation-value synthesis circuitry 207 included in the receiver circuitry 120 according to the first embodiment, respectively.

The calculation processing circuitry 300 performs a calculation process on multiple received signals obtained during multiple times of transmissions. For example, the calculation processing circuitry 300 acquires, from the received-signal memory 203, received signals obtained during multiple times of transmissions by modulating the amplitude or the phase, performs a calculation process on the received signals based on the AM method or the PM method, and extracts multiple harmonic components in each scan line. Then, the calculation processing circuitry 300 outputs the extracted harmonic components (received signals) to the transmit-wavefront correction circuitry 204. Here, the calculation processing circuitry 300 is an example of a calculating unit.

Thus, the transmit-wavefront correction circuitry 204 corrects the received signals having undergone the calculation process with a delay amount based on the propagation time of the transmit wavefront. Also, the synthesis circuitry 205 executes transmit aperture synthesis on the corrected received signals for coherent summation, and the phase evaluation circuitry 206 evaluates the degree of consistency between the phases of the corrected received signals to calculate an evaluation value. Then, the evaluation-value synthesis circuitry 207 corrects the received signal having undergone transmit aperture synthesis based on the evaluation value. Then, the B-mode processing circuitry 130 performs an envelope detection process, or the like, on the received signal of a harmonic component, thereby generating B-mode data. Then, the image generation circuitry 150 generates ultrasound image data from the B-mode data generated by the B-mode processing circuitry 130.

Figure 11:
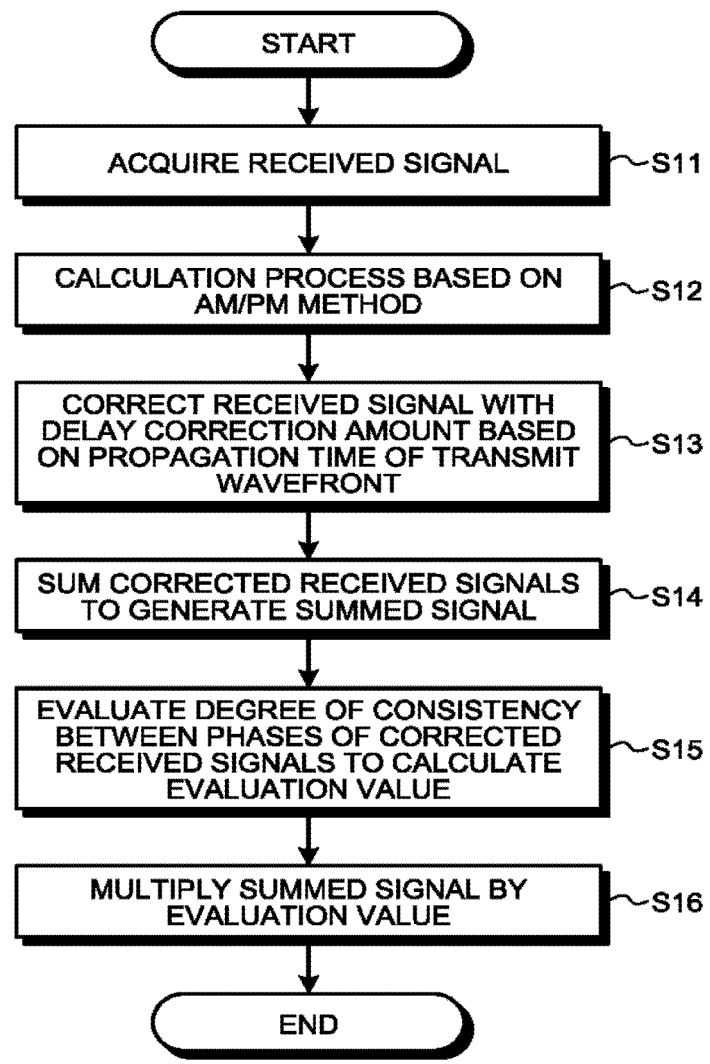
FIG. 11 is a flowchart that illustrates the steps of a transmit-aperture synthesis process by the receiver circuitry according to the second embodiment.

FIG. 11 is a flowchart that illustrates the steps of a transmit-aperture synthesis process by the receiver circuitry 120 according to the second embodiment. FIG. 11 illustrates the flowchart that explains operation of the receiver circuitry 120. Step S11 to Step S12 are steps performed by the calculation processing circuitry 300. At Step S11, the calculation processing circuitry 300 acquires a received signal from the received-signal memory 203. At Step S12, the calculation processing circuitry 300 performs a calculation process based on the AM/PM method.

Step S13 is a step performed by the transmit-wavefront correction circuitry 204. At Step S13, the transmit-wavefront correction circuitry 204 corrects a received signal with a delay correction amount based on the propagation time of the transmit wavefront. Step S14 is a step performed by the synthesis circuitry 205. At Step S14, the synthesis circuitry 205 sums the corrected received signals to generate a summed signal. Step S15 is a step performed by the phase evaluation circuitry 206. At Step S15, the phase evaluation circuitry 206 evaluates the degree of consistency between the phases of the corrected received signals to calculate an evaluation value. Step S16 is a step performed by the evaluation-value synthesis circuitry 207. At Step S16, the evaluation-value synthesis circuitry 207 multiplies the summed signal by the evaluation value.

As described above, according to the second embodiment, a calculation process is performed on multiple received signals obtained during multiple times of transmissions, and the received signals having undergone the calculation process are corrected with a delay amount based on the propagation time of the transmit wavefront. Then, according to the second embodiment, coherent summation is executed on the received signals that have been corrected with a delay amount based on the propagation time of the transmit wavefront after the calculation process. Furthermore, according to the second embodiment, the degree of consistency between the phases of the received signals, which have been corrected with a delay amount based on the propagation time of the transmit wavefront after the calculation process, is evaluated, and an evaluation value is calculated at each observation point. Then, according to the second embodiment, the received signal having undergone transmit aperture synthesis is corrected based on the evaluation value, and an ultrasound image is generated. Thus, according to the second embodiment, ultrasound images with an improved space resolution may be obtained.

Figure 12:
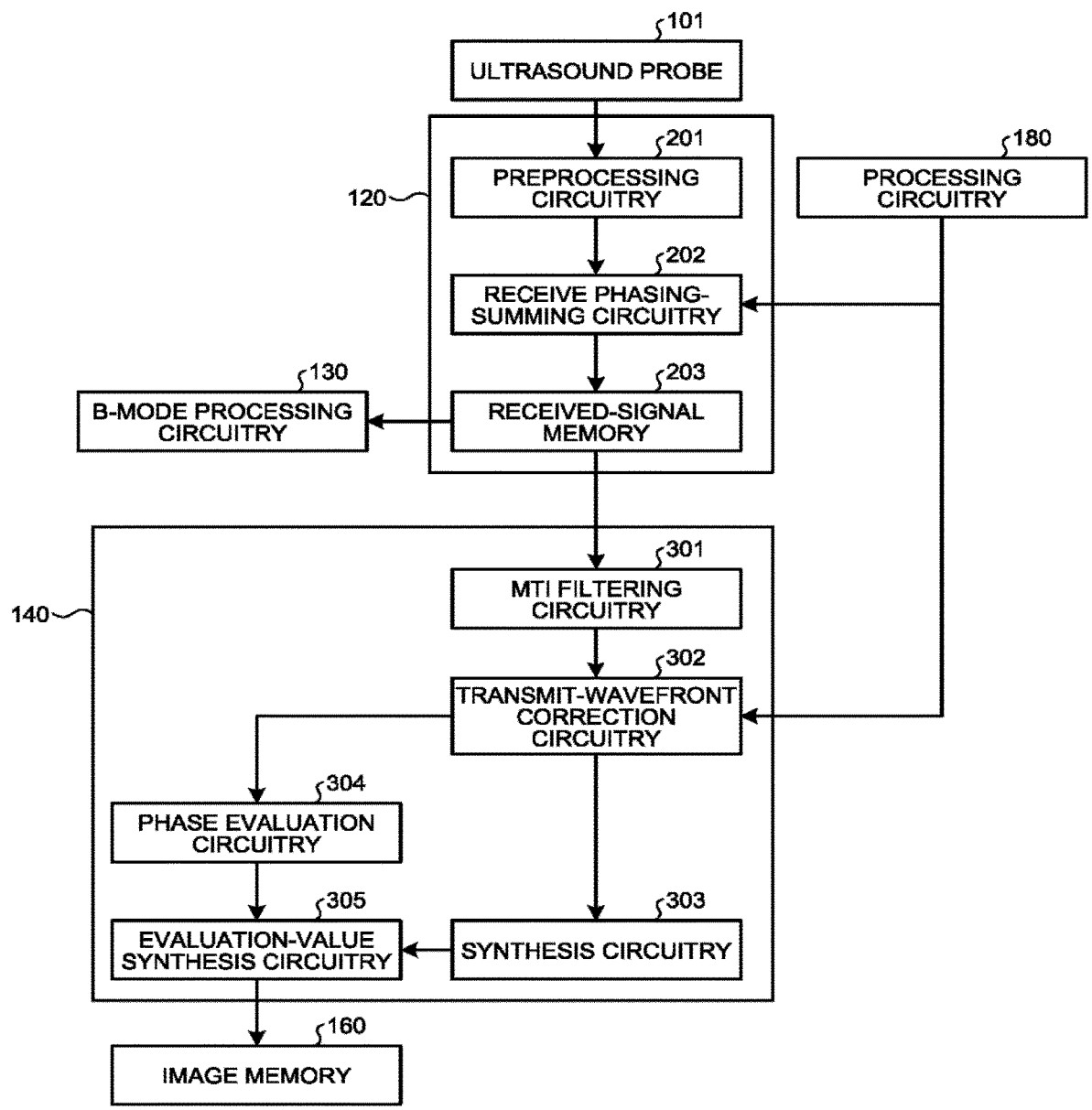
FIG. 12 is a block diagram that illustrates an example of the configuration of the receiver circuitry and Doppler processing circuitry according to a third embodiment.

In a third embodiment, an explanation is given of a case where a transmit-aperture synthesis process is applied to the blood-flow Doppler method. Furthermore, an example of the configuration of the ultrasound diagnostic apparatus according to the third embodiment is the same as the ultrasound diagnostic apparatus 1 according to the first embodiment illustrated in FIG. 1 except that the configurations of part of the receiver circuitry 120 and the Doppler processing circuitry 140 are different. FIG. 12 is a block diagram that illustrates an example of the configuration of the receiver circuitry 120 and the Doppler processing circuitry 140 according to the third embodiment.

As illustrated in FIG. 12, the receiver circuitry 120 according to the third embodiment includes the preprocessing circuitry 201, the receive phasing-summing circuitry 202, and the received-signal memory 203. The preprocessing circuitry 201, the receive phasing-summing circuitry 202, and the received-signal memory 203 included in the receiver circuitry 120 according to the third embodiment correspond to the preprocessing circuitry 201, the receive phasing-summing circuitry 202, and the received-signal memory 203, respectively, included in the receiver circuitry 120 according to the first embodiment. Specifically, the receiver circuitry 120 according to the third embodiment performs a phasing-summing process to generate reflected wave data and stores generated reflected wave data in the received-signal memory 203.

Furthermore, as illustrated in FIG. 12, the Doppler processing circuitry 140 according to the third embodiment includes MTI (moving target indicator) filtering circuitry 301, transmit-wavefront correction circuitry 302, synthesis circuitry 303, phase evaluation circuitry 304, and evaluation-value synthesis circuitry 305.

The MTI filtering circuitry 301 applies an MTI filter to multiple received signals. Here, the MTI filtering circuitry 301 uses a Butterworth IIR (infinite impulse response) filter, an MTI filter such as polynomial regression filter) with a fixed coefficient, or an adaptive MTI filter with a coefficient changed in accordance with an input signal. Here, the MTI filtering circuitry 301 is an example of an MTI filtering unit.

Thus, the transmit-wavefront correction circuitry 302 corrects multiple received signals, to which the MTI filter has been applied, with a delay amount based on the propagation time of the transmit wavefront in the same manner as the transmit-wavefront correction circuitry 204. Furthermore, the synthesis circuitry 303 executes transmit aperture synthesis on corrected received signals for coherent summation in the same manner as the synthesis circuitry 205, and the phase evaluation circuitry 304 evaluates the degree of consistency between the phases of the corrected received signals to calculate an evaluation value in the same manner as the phase evaluation circuitry 206. Here, the phase evaluation circuitry 304 does not set the amplitude as the evaluation target but sets only the phase as the evaluation target. Therefore, even in the case of Doppler data with a small amplitude, the phase evaluation circuitry 304 is capable of detecting misalignment in phases in the same manner as the phase evaluation circuitry 206. The evaluation-value synthesis circuitry 305 corrects a received signal having undergone transmit aperture synthesis based on an evaluation value in the same manner as the evaluation-value synthesis circuitry 207.

Then, the Doppler processing circuitry 140 generates data (Doppler data) by conducting frequency analysis on received signals for velocity information, extracting a blood current, tissue, or contrast-agent echo component due to the Doppler effect, and extracting movable object information, such as the average speed, variance, or power, at multiple points. Then, the image generation circuitry 150 generates ultrasound image data from Doppler data generated by the Doppler processing circuitry 140.

FIG. 13 is a flowchart that illustrates the steps of the transmit-aperture synthesis process by the Doppler processing circuitry 140 according to the third embodiment. FIG. 13 illustrates the flowchart that explains operation of the Doppler processing circuitry 140. Step S21 and Step S22 are steps performed by the MTI filtering circuitry 301. At Step S21, the MTI filtering circuitry 301 acquires a received signal from the received-signal memory 203. At Step S22, the MTI filtering circuitry 301 performs the MTI filtering processing on the received signal acquired at Step S21.

Step S23 is a step performed by the transmit-wavefront correction circuitry 302. At Step S23, the transmit-wavefront correction circuitry 302 corrects a received signal with a delay correction amount based on the propagation time of the transmit wavefront. Step S24 is a step performed by the synthesis circuitry 303. At Step S24, the synthesis circuitry 303 sums the corrected received signals to generate a summed signal. Step S25 is a step performed by the phase evaluation circuitry 304. At Step S25, the phase evaluation circuitry 304 evaluates the degree of consistency between the phases of the corrected received signals to calculate an evaluation value. Step S26 is a step performed by the evaluation-value synthesis circuitry 305. At Step S26, the evaluation-value synthesis circuitry 305 multiplies the summed signal by the evaluation value.

As described above, according to the third embodiment, the MTI filter is applied to multiple received signals, and the received signals, to which the MTI filter has been applied, are corrected with a delay amount based on the propagation time of the transmit wavefront. Then, coherent summation is executed on the received signals that have been corrected with a delay amount based on the propagation time of the transmit wavefront. Furthermore, according to the third embodiment, the degree of consistency between the phases of the received signals, which have been corrected with a delay amount based on the propagation time of the transmit wavefront, is evaluated, and an evaluation value is calculated at each observation point. Then, according to the third embodiment, a received signal having undergone transmit aperture synthesis is corrected based on the evaluation value, Doppler data is extracted, and an ultrasound image is generated based on the Doppler data. Thus, according to the third embodiment, ultrasound images with an improved space resolution may be obtained.

Embodiments are not limited to the above-described embodiments.

For example, the receiver circuitry 120 may apply filtering processing to received signals so as to enhance a desired frequency band. In such a case, the receiver circuitry 120 may have filtering circuitry for filtering processing at the stage before or after the receive phasing-summing circuitry 202. Furthermore, in such a case, the transmit-wavefront correction circuitry 204 corrects a received signal selected at a desired frequency band from received signals with a delay amount based on the propagation time of the transmit wavefront.

Furthermore, for example, the phase evaluation circuitry 206 may not only calculate the evaluation value of a predetermined frequency component but also calculate the evaluation value of each of different frequency components included in a received signal.

In the explanation according to the above-described embodiment, the phase evaluation circuitry 206 calculates evaluation values; however, this is not a limitation on embodiments. For example, the receiver circuitry 120 may include memory that previously stores an evaluation value that corresponds to a degree of consistency between phases. In such a case, the memory stores previously calculated evaluation values as a look-up table. Furthermore, evaluation values stored as a look-up table may be calculated by the processing circuitry 180. Then, the evaluation-value synthesis circuitry 207 determines the evaluation value that corresponds to a degree of consistency between the phases of received signals from the memory and corrects the received signal having undergone transmit aperture synthesis based on the evaluation value.

Furthermore, there are imaging methods called spatial compound by summing a group of received signals obtained while changing the transmit sound field for each transmission and reception and by summing a group of received signals obtained while changing the receive sound field. According to the methods, the transmit/receive sound field is changed by changing the position of the transmit focal point, the transmit aperture width, the position of the receive focal point, the receive aperture width, and the like, for each transmission and reception. According to the above-described embodiment, the methods may be implemented in combination. Specifically, the processing circuitry 180 may change at least any one of the position of the focal point of a transmitted ultrasound wave and the aperture width for transmitting an ultrasound wave in each of a predetermined number of times of ultrasound transmissions/receptions. In such a case, the transmit-wavefront correction circuitry 204 corrects multiple received signals obtained by changing at least any one of the receive aperture and the receive focus position with a delay amount based on the propagation time of the transmit wavefront.

The term "processor" used in the above explanation means, for example, a CPU (central processing unit), a GPU (graphics processing unit), or a circuit, such as an application specific integrated circuit (ASIC), a programmable logic device (e.g., a simple programmable logic device (SPLD), a complex programmable logic device (CPLD), or a field programmable gate array (FPGA)). The processor reads a program stored in memory and executes it, thereby implementing a function. Furthermore, instead of storing programs in the memory, a configuration may be such that programs are directly installed in circuitry of the processor. In this case, the processor reads the program installed in the circuitry and executes it, thereby implementing a function. Furthermore, with regard to each processor according to the present embodiment, each processor may not be always configured as single circuitry but also configured as a single processor by combining multiple independent circuitries so that its function is implemented. Furthermore, the components in FIG. 1 may be integrated into a single processor to implement its function.

In the above explanation of the embodiments, the components of each device illustrated are conceptual in functionality and do not necessarily need to be physically configured as illustrated in the drawings. Specifically, specific forms of separation and integration of each device are not limited to those depicted in the drawings, and a configuration may be such that all or some of them are functionally or physically separated or integrated in any unit in accordance with various types of loads, usage, or the like. Furthermore, all or any of various processing functions performed by each device may be implemented by a CPU and a program analyzed and executed by the CPU or may be implemented by wired logic hardware.

The image processing method that is described in the above embodiment may be performed when a prepared image processing program is executed by a computer such as personal computer or workstation. The image processing program may be distributed via a network such as the Internet. The image processing program may be recorded on a recording medium readable by a computer, such as hard disk, flexible disk (FD), CD-ROM, MO, or DVD, and may be executed by being read from the recording medium by the computer.

According to at least one of the embodiments described above, the image quality may be improved.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasound diagnostic apparatus, comprising:
processing circuitry configured to
execute transmit aperture synthesis to conduct coherent summation on multiple received signals that are at different transmit apertures and in an identical scan line,
evaluate a degree of consistency between phases of the received signals to calculate an evaluation value at each observation point such that the evaluation value increases as the degree of consistency between the phases increases, wherein the evaluation value is calculated for each of different frequency components included in the received signal of the multiple received signals, and
correct a received signal of the multiple received signals having undergone the transmit aperture synthesis based on the calculated evaluation value.

2. The ultrasound diagnostic apparatus according to claim 1, wherein the processing circuitry is further configured to correct the multiple received signals with a delay amount based on a propagation time of a transmit wavefront to produce delay-corrected received signals,
execute the transmit aperture synthesis to conduct coherent summation on the delay-corrected received signals,
evaluate a degree of consistency between phases of the delay-corrected received signals to calculate a delay-corrected evaluation value as the evaluation value, and
correct the received signal of the multiple received signals having undergone the transmit aperture synthesis based on the delay-corrected evaluation value.

3. The ultrasound diagnostic apparatus according to claim 2, wherein the processing circuitry is further configured to correct the received signal selected at a desired frequency band from the multiple received signals with the delay amount based on the propagation time of the transmit wavefront.

4. The ultrasound diagnostic apparatus according to claim 1, wherein the processing circuitry is further configured to change at least any one of a position of a focal point of a transmitted ultrasound wave and an aperture width for transmitting an ultrasound wave at each of a predetermined number of times of transmission and reception of an ultrasound wave.

5. The ultrasound diagnostic apparatus according to claim 2, wherein the processing circuitry is further configured to
conduct multiple times of transmissions by modulating an amplitude or a phase of an ultrasound wave to be transmitted,
perform a calculation process on plural of the multiple received signals obtained during the multiple times of transmissions, and
correct the plural of the multiple received signals having undergone the calculation process with the delay amount.

6. The ultrasound diagnostic apparatus according to claim 5, wherein the processing circuitry is further configured to change at least any one of a position of a focal point of a transmitted ultrasound wave and an aperture width for transmitting an ultrasound wave at each of a predetermined number of times of transmission and reception of an ultrasound wave.

7. The ultrasound diagnostic apparatus according to claim 2, wherein the processing circuitry is further configured to correct plural of the multiple received signals obtained by changing at least any one of a receive aperture and a receive focus position with a delay amount based on a propagation time of a transmit wavefront.

8. The ultrasound diagnostic apparatus according to claim 2, wherein the processing circuitry is further configured to apply an MTI filter to the multiple received signals and correct the multiple received signals having the MTI filter applied thereto with the delay amount.

9. The ultrasound diagnostic apparatus according to claim 1, further comprising a memory that previously stores an evaluation value that corresponds to a degree of consistency between phases, wherein
the processing circuitry is further configured to determine an evaluation value that corresponds to a degree of consistency between phases of the multiple received signals from the memory and correct the received signal of the multiple received signals having undergone the transmit aperture synthesis based on the evaluation value.

10. A medical image processing apparatus, comprising:
processing circuitry configured to
execute transmit aperture synthesis to conduct coherent summation on multiple received signals that are at different transmit apertures and in an identical scan line,
evaluate a degree of consistency between phases of the received signals to calculate an evaluation value at each observation point such that the evaluation value increases as the degree of consistency between the phases increases, wherein the evaluation value is calculated for each of different frequency components included in the received signal of the multiple received signals, and
correct a received signal of the multiple received signals having undergone the transmit aperture synthesis based on the calculated evaluation value.

11. A medical image processing method, comprising:
executing transmit aperture synthesis to conduct coherent summation on multiple received signals that are at different transmit apertures and in an identical scan line;
evaluating a degree of consistency between phases of the received signals to calculate an evaluation value at each observation point such that the evaluation value increases as the degree of consistency between the phases increases, wherein the evaluating step further comprises calculating the evaluation value for each of different frequency components included in the received signal of the multiple received signals; and
correcting a received signal of the multiple received signals having undergone the transmit aperture synthesis based on the calculated evaluation value.

12. The ultrasound diagnostic apparatus according to claim 1, wherein the processing circuitry is further configured to receive the multiple received signals from different oscillating elements of an ultrasound probe.

13. The medical image processing apparatus according to claim 10, wherein the processing circuitry is further configured to receive the multiple received signals from different oscillating elements of an ultrasound probe.

14. The medical image processing method according to claim 11, further comprising receiving the multiple received signals from different oscillating elements of an ultrasound probe.

15. An ultrasound diagnostic apparatus, comprising:
processing circuitry configured to
execute transmit aperture synthesis to conduct coherent summation on multiple received signals that are at different transmit apertures and in an identical scan line,
evaluate a degree of consistency between phases of the received signals to calculate an evaluation value at each observation point, and
correct, without using inverse matrix calculations, a received signal having undergone the transmit aperture synthesis such that the corrected received signal increases as the evaluation value increases.

16. The ultrasound diagnostic apparatus according to claim 15, wherein the processing circuitry is further configured to correct the received signal having undergone the transmit aperture synthesis by multiplying the evaluation value by the received signal having undergone the transmit aperture synthesis.

17. The ultrasound diagnostic apparatus according to claim 15, wherein the processing circuitry is further configured to correct the received signal having undergone the transmit aperture synthesis by adding the evaluation value and the received signal having undergone the transmit aperture synthesis after they are multiplied by a coefficient.

18. The ultrasound diagnostic apparatus according to claim 15, wherein the processing circuitry is further configured to set a higher value as the evaluation value as the degree of consistency between the phases is higher.

* * * * *